United States Patent [19]
DiCarolis

[11] Patent Number: 5,412,129
[45] Date of Patent: May 2, 1995

[54] STABILIZATION OF PRECURSORS FOR THIN FILM DEPOSITION

[76] Inventor: Stephen A. DiCarolis, 2212 Cabrillo Ave., Santa Clara, Calif. 94304

[21] Appl. No.: 261,572

[22] Filed: Jun. 17, 1994

[51] Int. Cl.⁶ .................. C07F 1/00; C07F 15/04; C07F 15/06; C07F 3/06
[52] U.S. Cl. .................. 556/40; 556/146; 556/45; 556/117; 556/130; 427/248.1
[58] Field of Search .................. 556/40, 45, 117, 130, 556/146

[56] References Cited

U.S. PATENT DOCUMENTS 3,911,176  10/1975  Curtis et al. .................. 427/248

OTHER PUBLICATIONS

J. A. T. Norman et al. "Volatile Barium, Strontium and Calcium Bis(hexafluoroacetylacetonate)(crown ether) Complexes", 1991, pp. 971-972, *J. Chem. Soc., Chem. Commun.*

Klass Timmer et al. "Synthesis and characterization of BaX₂.18-crown-6 complexes. Barium bis(1,1,1,5,5,5-hexafluoropentate-2,4-dionate).18-crown-6, a non-hygroscopic, thermally stable, volatile barium compound." 1991, vol. 187, pp. 99-106, *Inorg. Chim. Acta.*

George S. Hammond et al. "Chelates of β-Diketones. V. Preparation and Properties of Chelates Containing Sterically Hindered Ligands", Feb. 1963, vol. 2 (1), pp. 73-76, *Inorganic Chemistry*.

R. Hiskes et al. "Single source metalorganic chemical vapor deposition of low microwave surface resistance YBa₂Cu₃O₇", 29 Jul. 1991, vol. 59(5), pp. 606-607. *Applied Physics Letters*.

Alex A. Wernberg et al. "MOCVDDeposition of Epitaxial LiNbO₃ Thin Films Using the Single-Source Precursor LiNb(OEt)₆", 1993, vol. 5 (8), pp. 1056-1058, *Chem. Mater.*

B. J. Curtis et al. "The Growth of Thim Films of Lithium niobate by Chemical Vapour Deposition", 1975, vol. 10, pp. 515-520, *Mat. Res. Bull.*

*Primary Examiner*—José G. Dees
*Assistant Examiner*—Porfirio Nazario-Gonzalez

[57] ABSTRACT

A precursor used in an MOCVD reactor for production of thin films of certain metal oxides is stabilized by introducing a ligand into the precursor during the precursor synthesis and thereby protecting the precursor from premature oxidation, nucleation, and decomposition.

10 Claims, No Drawings

STABILIZATION OF PRECURSORS FOR THIN FILM DEPOSITION

BACKGROUND OF THE INVENTION

This invention relates generally to techniques for thin film deposition, and more particularly, to techniques for stabilizing precursors to produce thin films.

Thin film deposition, using MOCVD (metal organic chemical vapor deposition), is an important fabrication method for a variety of electrical and electro-optical materials, for example, super conductor materials and optical wave guides. Some MOCVD reactors sublime one or more solid precursors and transport the resulting vapor in an inert carrier gas to a heated substrate upon which certain chemical reactions occur resulting in the deposition of a thin film product.

Lithium Niobate ($LiNbO_3$) is an electro-optic ceramic which may be prepared using one of a variety of methods, including MOCVD, as described by Wernberg, A. A., and Gysling, H. J., *MOCVD Deposition of Epitaxial $LiNbO_3$ Thin Films Using the Single-Source Precursor $LiNb(O\ Et)_6$*. The reference lists numerous manufacturing methods for $LiNbO_3$ including MOCVD methods. For example, $LiNbO_3$ has hitherto been manufactured in a two-source MOCVD process using lithium 2,2,6,6-tetramethylheptane-3,5-dionate (Li(thd)) and $Nb(OMe)_5$. MOCVD fabrication of $LiNbO_3$ is also described in U.S. Pat. No. 3,911,176, to Curtis et al., entitled "Method for Vapor-phase Growth of Thin Films of Lithium Niobate" wherein a substrate of Lithium tantalate ($LiTaO_3$) is coated with a thin film of $LiNbO_3$ obtained from Li(thd) and $Nb(OMe)_5$ precursors.

Additionally, $LiNbO_3$ has been manufactured by a MOCVD process using a toluene solution of a single-source precursor generated in situ by the reaction of $Nb(OEt)_5$ and Li(thd).

A third method of manufacturing $LiNbO_3$, reported by Wernberg and Gysling, uses a single-source reagent, $LiNb(OEt)_6$, in a spray MOCVD process.

A fourth method of manufacturing $LiNbO_3$ is a two-source solid precursor MOCVD process using Li(thd) and $Nb(thd)_4$ precursors.

A number of difficulties exist with these methods of manufacturing $LiNbO_3$. In the case of the first method, the method produces a film which is polycrystaline and black, therefore unsuitable for optical applications; the second method produces a rough surface; the third method have a certain amount of defects in the film surface due to the gas phase decomposition of the precursor; and the fourth method suffers from the premature oxidation of the Li(thd). This premature oxidation produces a lithium carbonate soot which is deposited into the thin film, thereby degrading the optical quality as well as reducing the growth rate of the film. Furthermore, it has been found that this method requires a 7-to-3 ratio of Li(thd) to Nb(thd) although the stoichiometry leads to a 1-to-1 expected ratio.

Two types of precursor thermal stability are of concern in MOCVD reactions. The first kind is the thermal stability of the precursor as it is being sublimed and transported in the carrier gas to the substrate. The second kind of thermal stability is the precursor stability in the very hot vicinity of the substrate.

The substrate in a MOCVD reactor for producing $LiNbO_3$ is approximately 700° C. Li(thd) is thermally stable to about 400° C. The lithium carbonate soot is produced by oxidation of a certain amount of the Li(thd) in the hot vicinity of the substrate. The lithium carbonate is then deposited onto the substrate and is absorbed into the thin film.

A prior approach to solving this problem is to use commercially available Li(thd) prepared by the method described in Hammond, G. S, Nonhebel, D. C., and Wu, C-W. S., *Inorg. Chem.*, 2, 73 (1963). The quantity of soot is minimized by reducing the deposition temperature of the film onto the substrate, thereby reducing the overall reactor temperature. However, there is nevertheless an unacceptable quantity of soot absorbed into the $LiNbO_3$ film. Furthermore, the low deposition temperatures result in films with less than optimum crystalline properties.

In light of the foregoing, it is desirable to have a solid source MOCVD process for producing a high quality thin film $LiNbO_3$ with no defects, no soot particles, and a required ratio of precursor quantities which approximates the stoichiometrically expected ratio.

There has been certain attempts in the prior art to chemically stabilize the precursors used in various MOCVD reactions. However, these prior art attempts focus on the first kind of precursor stability (i.e., stability during sublimation).

A number of stabilized complexes of the precursor for alkaline earth compounds used in the chemical vapor deposition of certain superconducting oxides, such as Y-Ba-Cu, Bi-Sr-Ca-Cu and Tl-Ba-Ca-Cu oxides are described in Timmer, K., and Meinema, H. A., Synthesis and characterization of $BaX_2$18-crown-6 complexes. Barium bis(1,1,1,5,5,5-hexafluoropentane-2,4-dionate)18-crown-6, a non-hygroscopic, thermally stable, volatile barium compound, *Inorg. Chem. Acta*, Vol. 187, pp. 99–106 (1991). Therein is described, for example, the preparation of Ba(thd)-18-crown-6. In the reference it was noted that Barium-$\beta$-diketonates, used as precursors for the synthesis of thin films of $YBa_2Cu_3O_{7-x}$, are prone to oligomerization and decomposition at the temperatures required to obtain the volatility necessary for MOCVD processes. However, the reference notes that complexes between Barium hexafluoropentane dionate including an 18-crown-6 ligand are volatile at lower temperatures and thermally stable at those temperatures. In Norman, J. A. T., and Pez, G. P., "Volatile Barium, Strontium and Calcium Bis(hexafluoroacetylacetenate)(crown ether) Complexes", J. Chem. Soc., Chem. Commun., pp. 971–972 (1991) similar properties are observed, also for Alkaline earth diketonate complexes with crown-ethers. However, the references do not discuss the thermal properties of the precursor near the substrate and do not discuss stabilization of non-alkaline earth compounds used in MOCVD reactions.

An additional problem found when using unstable precursors is the deposition of material on the reactor walls upstream from the substrate.

Accordingly, it would be desirable to stabilize the precursors for the production of alkali metal-containing oxides to avoid the premature oxidation, gas phase nucleation, and decomposition of the precursors, and thereby improve the quality of the thin films produced by MOCVD processes.

SUMMARY OF THE INVENTION

Generally, in one form of the invention, a precursor used in an oxidizing MOCVD reactor is stabilized by introducing therein a neutral stabilizing ligand. The ligand is introduced during the synthesis of the precursor and coordinately bonds to a metal cation in the precursor. The entire complex becomes more stable and therefore less prone to premature oxidation, nucleation, and decomposition.

In one embodiment the invention is used to stabilize a lithium 2,2,6,6-tetramethyl-3,5-heptanedionate (Li(thd)) by incorporating thereto 18-crown-6. The resulting complex is used together with Niobium 2,2,6,6-tetramethyl-3,5-heptanedionate (Nb(thd)) in an MOCVD reactor to produce thin film $LiNbO_3$.

In a second embodiment of the invention K(thd) is stabilized in the same fashion.

It is an object of the invention to stabilize a precursor used in an MOCVD oxidizing reactor to prevent the premature oxidation of the precursor, gas phase nucleation, and decomposition by introducing a neutral stabilizing ligand into the precursor.

It is an object of the invention to improve the precursors used in the preparation of thin films of various compounds.

DETAILED DESCRIPTION OF THE PREFERRED EMBODIMENTS

The present invention will now be described in detail.

1. General Formula for Stabilized Alkali Metal MOCVD Precursor

Examples of the chemical composition of a precursor according to the present invention for producing high quality thin film of various compounds using MOCVD reactions include the following:

M—E—T wherein:

M is a metal cation selected from the group including the alkali metals,

E is a crown-ether, for example, selected from the group 18-crown-6, 12-crown-4, and 15-crown-5, and T is a dipivaloylmethane, for example, 2,2,6,6-tetramethyl-3,5-heptanedionate (thd).

The M—E—T complex is used as a first precursor in an oxide MOCVD reactor together with a second precursor having the formula M'—T' wherein M' is another metal cation and T' is either the same dipivaloylmethane as T or another diketone. Examples of M include Li and K; and examples of E include 18-crown-6, 15-crown-5, and 12-crown-4.

2. Preparation of $LiNbO_3$ and Other Alkali Metal Oxides

Lithium Niobate ($LiNbO_3$) and other alkali metal oxides may be manufactured using metalorganic chemical vapor deposition, for example, in an apparatus similar to the apparatus described in Hiskes, R., DiCarolis, S. A., Fouquet, J., Lu, Z., Feigelson, R. S., Route, R. K., Leplingard, F., and C. M. Foster, Proceedings of the MRS Fall Meeting, Dec. 1993.

In one embodiment of the invention, in the MOCVD preparation of an alkalimetal oxide, for example $LiNbO_3$, alkali metal dipivaloylmethanates (also known as tetra methyl heptanedionates (thd)) are used as precursors. For example, in the preparation of $LiNbO_3$, Li(thd) and Nb(thd) are used as precursors.

The alkali-metal thd precursor is thermally stabilized by incorporating an additional neutral ligand, a crown ether, into the compound. To produce $LiNbO_3$, the Li(thd) precursor is stabilized by introducing 18-crown-6, 12-crown-4, 15-crown-5, or another crown-ether, into the compound.

The crown-ether ligand strongly binds to the alkali metal cation, thereby rendering the compound as a whole more resistant to premature gas phase oxidation while it is heated to the substrate deposition temperature.

3. Preparation of Alkali Metal Dipivaloylmethanate.Crown-Ether Adducts

The crown-ether ligand is introduced into the alkali metal dipivaloylmethanate during the preparation thereof. To produce lithium thd, a mixture of metallic lithium with a 5% molar excess of thd and a 5% molar excess of 18-crown-6 dissolved in toluene is refluxed for 24 hours. The refluxing dissolves approximately 95% of the lithium metal.

Next the mixture is cooled and the solvent, toluene, is stripped away under a stream of dry nitrogen, yielding a white waxy solid. This white waxy solid is a mixture of Li(thd), 18-crown-6, and the adduct Li(thd)-18-crown-6. The white waxy solid can be used without further purification in a MOCVD reactor together with Nb(thd) to produce $LiNbO_3$.

4. Schematic of Reaction for Preparation of Alkali Metal Dipivaloylmethanates Crown-Ether Adducts The reaction follows the following general formula:

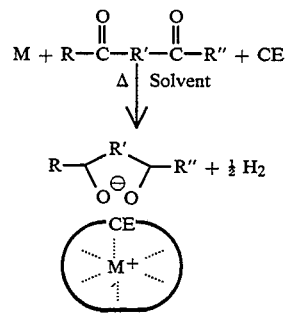

wherein,

M is a solid metal and $M^+$ is the corresponding cation;

R, R', and R" are hydrocarbon radicals; and

CE is a crown ether.

Specifically, the reaction for preparing Li(thd)-18-crown-6 is illustrated below:

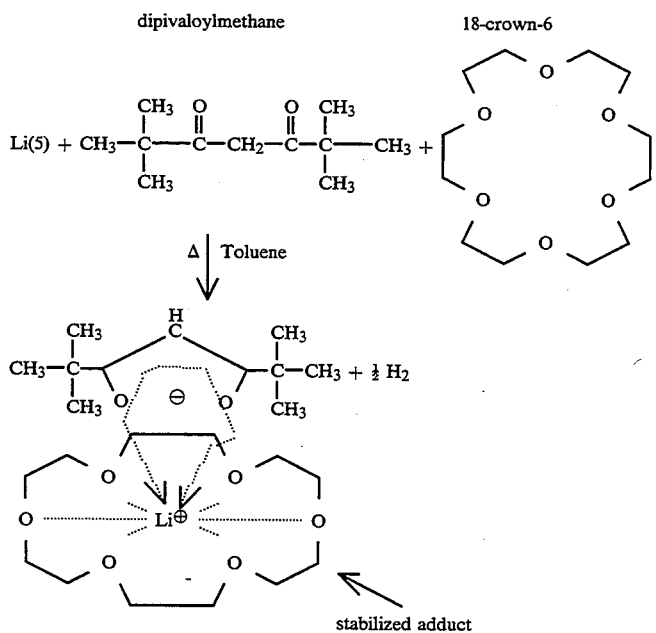

The 18-crown-6 ligand coordinately bonds to the metal cation thereby stabilizing the entire structure and preventing premature gas phase oxidation and gas phase nucleation.

The above described procedure may be utilized to form other stabilized adducts for MOCVD process precursors. For example, other than using potassium rather than lithium, the process for preparing potassium 2,2,6,6-tetramethyl-3,5-heptanedionate.18-crown-6 is identical to the process for preparing lithium(thd)18-crown-6 described above. Used in an MOCVD process for manufacturing potassium niobate ($KNbO_3$), the K(thd)18-crown-6 adduct is much superior to K(thd). Whereas the latter exhibits poor transportation of potassium to the reaction zone, the transportation of potassium to the reaction zone can be visually observed when using the K(thd)18-crown-6 adduct produced according to the above described procedure.

When the 18-crown-6 adducts of the alkali metal dipivaloylmethanates are used as sources in oxide MOCVD reactions, higher quality alkali metal oxide-containing films are obtained than those obtained from alkali metal dipivaloylmethanates precursors without the crown-ether ligand. The resultant films are relatively free from defects and particulates. Furthermore, the reactor walls upstream to the reactor are free from deposits. The films are of higher quality because of the avoidance of gas phase oxidation, nucleation, and decomposition.

The foregoing description of the preferred embodiment of the invention describes the use of 18-crown-6 as a ligand for stabilizing Li(thd). Li, 18-crown-6, and thd may all be substituted with analogous elements and chemicals. For example, the above described technique may be used with Tantalum(thd), and any number of crown-ethers may be used, e.g., 15-crown-5 and 12-crown-4.

What is claimed is:

1. An adduct of the formula:

M—E—T wherein

M is a cation of an element selected from the group consisting of alkali metals, copper, nickel, cobalt, manganese, and zinc;

E is a crown ether; and

T is an anion of a diketone.

2. The adduct of claim 1, wherein T is selected from the group having the formula

R(CO)R'(CO)R"

wherein R, R', and R" are hydrocarbon radicals.

3. The adduct of claim 2, wherein R and R" are the same radicals.

4. The adduct of claim 1, wherein T is 2,2,6,6-tetramethyl-3,5-heptanedionate.

5. The adduct of claim 1, wherein E is selected from the group 18-crown-6, 15-crown-5, and 12-crown-4.

6. The adduct of claim 1, wherein M is lithium.

7. The adduct of claim 1, wherein M is potassium.

8. A method of manufacturing an adduct of the formula

M—E—T wherein

M is a cation of an element selected from the group consisting of alkali metals, copper, nickel, cobalt, manganese, and zinc;

E is a crown ether; and

T is an anion of a diketone, comprising the steps of:

A. producing a mixture of metallic M with T and E in a solvent;

B. refluxing the mixture; and

C. stripping away the solvent.

9. The method of claim 8, wherein said refluxing step spans a period exceeding 18 hours.

10. The method of claim 9, wherein said refluxing step spans a period approximately 24 hours in duration.

* * * * *